(12) United States Patent
Rigon et al.

(10) Patent No.: US 6,379,335 B1
(45) Date of Patent: Apr. 30, 2002

(54) DEVICE FOR AFTER-USE PROTECTION OF A HYPODERMIC NEEDLE, PARTICULARLY OF THE BUTTERFLY TYPE

(75) Inventors: Francesco Rigon, Roverto S/S di Novi; Giorgio Mezzoli, Lugo, both of (IT)

(73) Assignee: D.R.M. S.r.l., Poggio Rusco (IT)

( * ) Notice: Subject to any disclaimer, the term of this patent is extended or adjusted under 35 U.S.C. 154(b) by 0 days.

(21) Appl. No.: 09/414,538

(22) Filed: Oct. 8, 1999

(30) Foreign Application Priority Data

Oct. 12, 1998 (IT) ........................................ BO98A0572

(51) Int. Cl.⁷ ............................ A61M 5/32; A61M 5/00; A61M 5/178
(52) U.S. Cl. .................. 604/177; 604/110; 604/164.08; 604/192; 604/263
(58) Field of Search ........................... 604/110, 164.08, 604/171, 177, 192, 198, 263, 174; 128/919

(56) References Cited

U.S. PATENT DOCUMENTS

| | | | |
|---|---|---|---|
| 5,192,275 A | * | 3/1993 | Burns |
| 5,219,339 A | | 6/1993 | Saito |
| 5,562,636 A | * | 10/1996 | Utterberg |
| 5,651,772 A | | 7/1997 | Arnett |
| 5,921,969 A | * | 7/1999 | Vallelunga et al. |

FOREIGN PATENT DOCUMENTS

WO 97 25082 7/1997

\* cited by examiner

*Primary Examiner*—Michael J Hayes
(74) *Attorney, Agent, or Firm*—Guido Modiano; Albert Josif; Daniel O'Byrne

(57) ABSTRACT

A device for after-use protection of a hypodermic needle, particularly of the butterfly type, comprising an elongated flat laminar element having, at one end and on two sides, two laminas which are mutually spaced by a longitudinal central space and are folded toward the laminar element in order to form two blind lateral flat guides for the sliding of the butterfly wings of the needle. The blind lateral flat guides are slightly curved away from the surface of the element and are adapted, when the needle retracts, to press its point so that it slides against the surface of the central band of the element in order to wedge into spaces that lie between raised saw-toothed teeth on the band in order to prevent the escape of the needle.

6 Claims, 4 Drawing Sheets

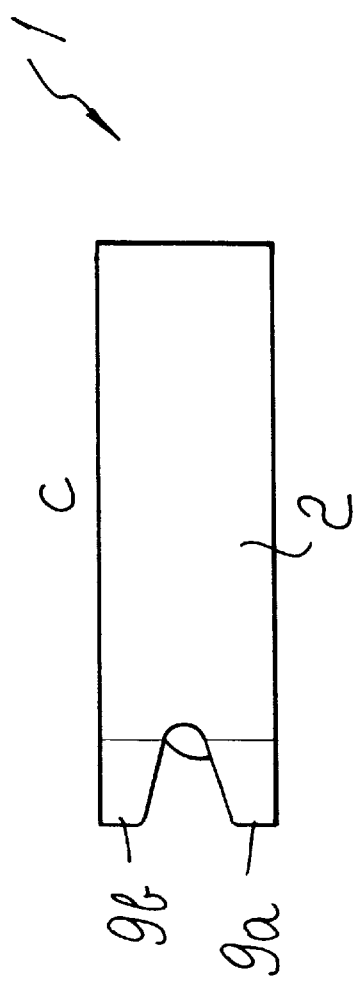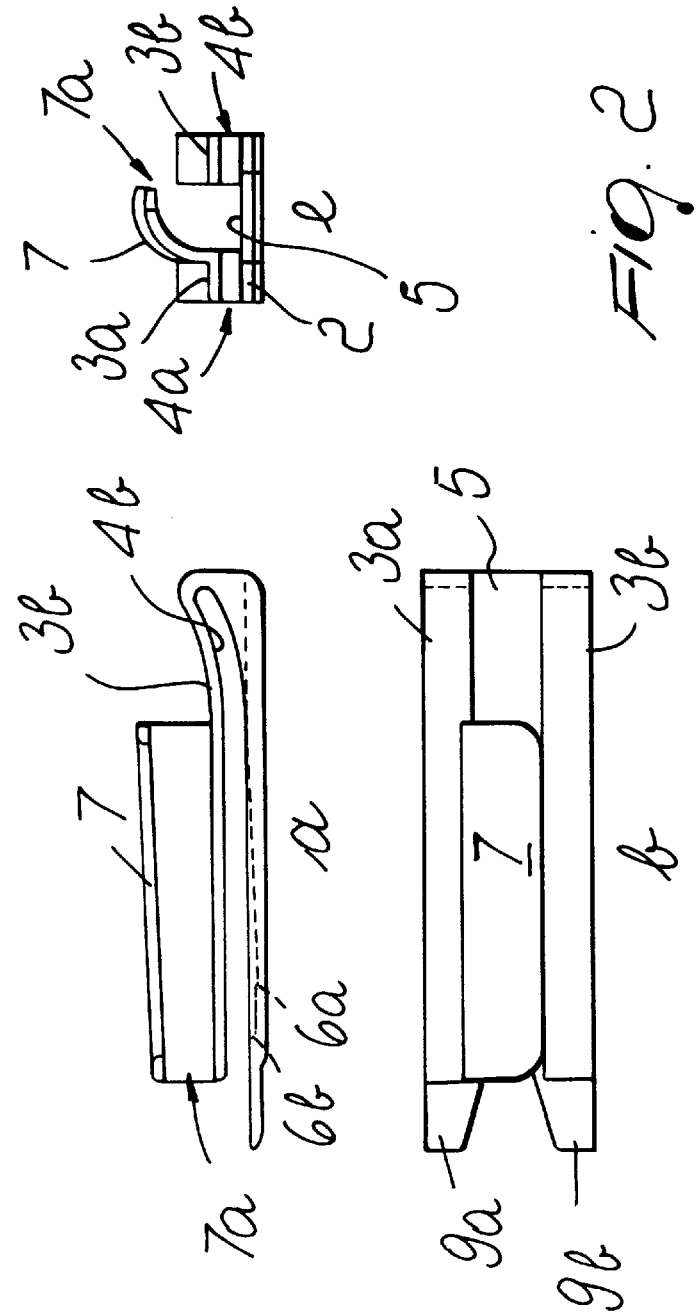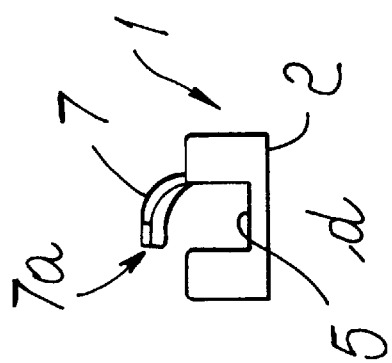
Fig. 2

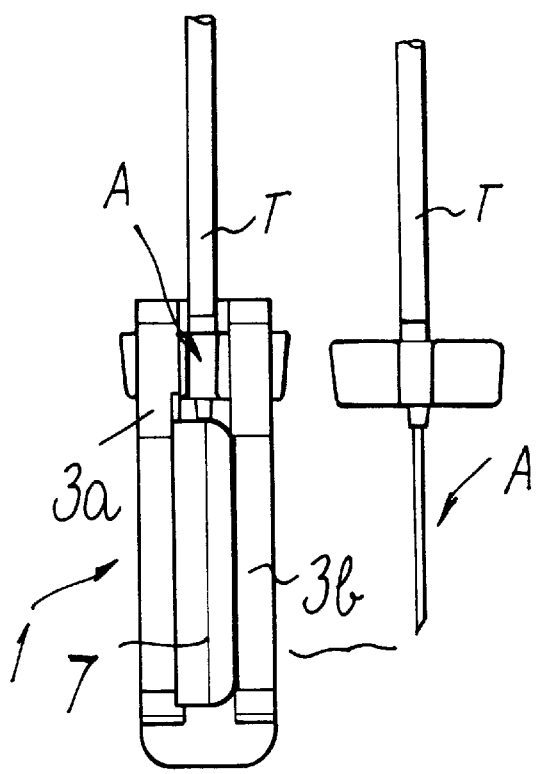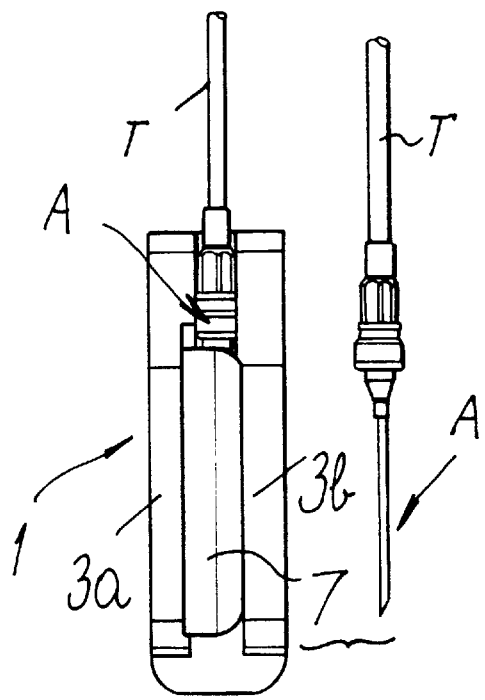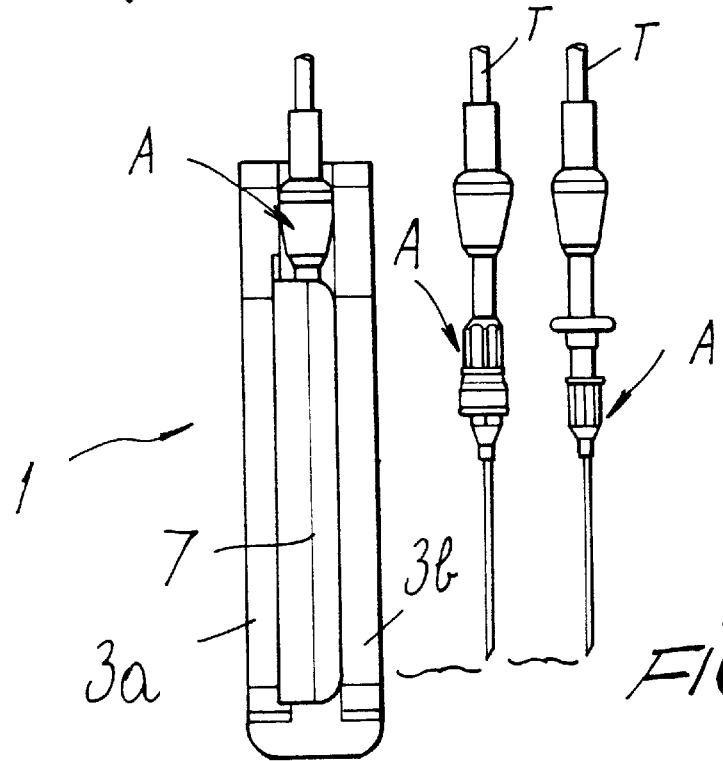

DEVICE FOR AFTER-USE PROTECTION OF A HYPODERMIC NEEDLE, PARTICULARLY OF THE BUTTERFLY TYPE

BACKGROUND OF THE INVENTION

The present invention relates to a device for after-use protection of a hypodermic needle, particularly of the butterfly type.

So-called butterfly needles are known which are used in the medical field to perform phleboclyses, transfusions, perfusions, sample-taking or the like.

Said needles derive their name from the fact that they are provided with a grip region shaped like co-planar butterfly wings and are fitted at the end of a tube which can be connected hydraulically to a bottle or to a bag for dispensing or withdrawing body liquids; when the wings are folded together, the grip region allows to easily insert the needle under the skin, and once the needle has been inserted and the wings have been released, it is meant to be surmounted by a portion of adhesive bandage which rigidly couples the needle to the patient and prevents its extraction.

These conventional needles entail a high risk of infection because they have the severe drawback that once removed from the patient their pointed end is not protected; in practice, medical or paramedic staff, when removing the needle, discards it together with the remaining material into polythenelined cardboard containers which can be perforated by said needles.

The staff performs such operations repeatedly, and in the course of time acquires ever greater confidence, often neglecting the necessary precautions; accordingly, sometimes the medical or paramedic staff suffers punctures while handling these used needles.

The consequent extremely severe danger of contamination, even with devastating diseases such as viral hepatitis or worse still AIDS, is evident.

Consequently, tubular rigid cases have been devised which are slid along the tube toward the needle and in which the needle is caught; the needle can no longer be removed due to the presence of hooks or snap-acting retention means on the two diametrically opposite sides of the case, which lock the two wings of the needle.

Conventional tubular cases have the drawback that they must be fitted on the tube at the factory: sliding the case along the tube further requires a plurality of manual movements which are very troublesome and awkward to perform, especially if they have to be performed with just one hand.

Moreover, the tubular shape of the cases does not allow to effectively press with cotton wool or the like simultaneously against the skin area perforated by the needle, against the needle and against the tubular case so as to block it during the extraction of the needle in order to avoid undue bleeding and thus allow to make the butterfly needle slide within the tubular protective case.

SUMMARY OF THE INVENTION

The aim of the present invention is to obviate the above drawbacks of conventional devices, i.e., to provide a device for after-use protection of a hypodermic needle, particularly of the butterfly type, which does not have to be fitted on the tube before the needle punctures the patient and which entails, for fitting on the tube, the execution of elementary movements which are easy even if they are performed with just one hand; it also allows to effectively press with cotton wool or the like against the skin area perforated by the needle during its extraction, in order to avoid bleeding, and to slide the needle into the device in the position for protecting the tip of the needle by working with just one hand.

If it is necessary to use the needle in a position in which space or other constraints do not allow to use the device by fitting it on the tube at the needle, the device can be fitted on the tube at a distance from the needle which is sufficient to avoid being in the way; once the needle has been removed from the skin of the patient, the device is retained with one hand and the tube is retracted with the other hand until the needle slides into the device in the position for protecting the tip.

Within the scope of this aim, an object of the present invention is to achieve said aim with a structure which is simple, relatively easy to provide in practice, safe in use, effective in operation and has a relatively low cost.

This aim and this object are both achieved by the present device for after-use protection of a hypodermic needle, particularly of the butterfly type, characterized in that it is constituted by an elongated flat laminar element having, at one end and on two sides, two laminas which are mutually spaced by a longitudinal central space and are folded toward the laminar element in order to form two blind lateral flat guides for the sliding of the butterfly wings of the needle; and in that said blind lateral flat guides are slightly curved away from the surface of the element and are adapted, when the needle retracts, to press its point so that it slides against the surface of the central band of the flat element in order to wedge into the bottom of the space that lies between two raised or flush saw-toothed protrusions or teeth of said band and prevent the escape of said needle.

BRIEF DESCRIPTION OF THE DRAWINGS

Further particularities will become apparent and evident from the detailed description of a preferred but not exclusive embodiment of a device for after-use protection of a hypodermic needle, particularly of the butterfly type, according to the invention, illustrated only by way of non-limitative example in the accompanying drawings, wherein:

FIGS. 2a, 2b, 2c, 2d, 2e are a front elevation view, a top plan view, a bottom plan view, a right side elevation view and a left side elevation view of the device;

FIGS. 3, 4 and 5 are plan views of the device according to the invention with different needles inserted (the respective needles are shown to the side);

DESCRIPTION OF THE PREFERRED EMBODIMENTS

Figure 1:
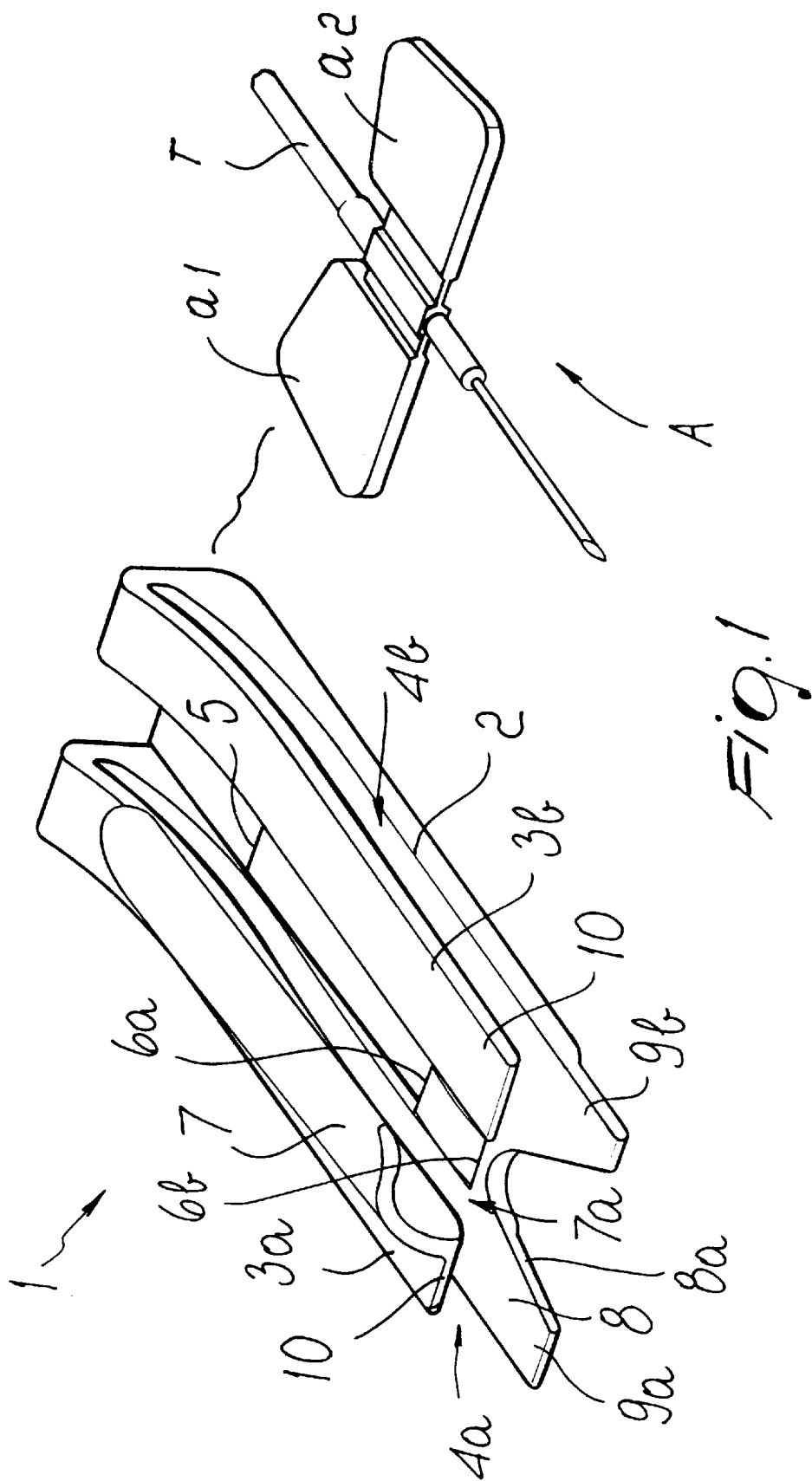
FIG. 1 is a perspective view of a device for after-use protection of a hypodermic needle, particularly of the butterfly type according to the invention, with the needle located externally.
Figure 6:
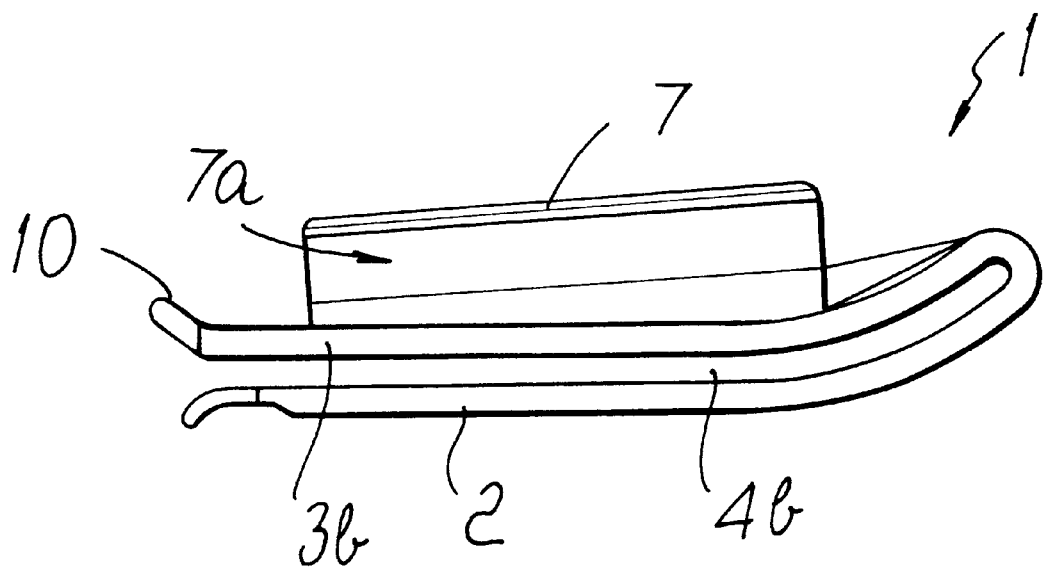
FIGS. 6 and 7 are two orthographic projection views of the real configuration of the device according to the invention.
Figure 7:
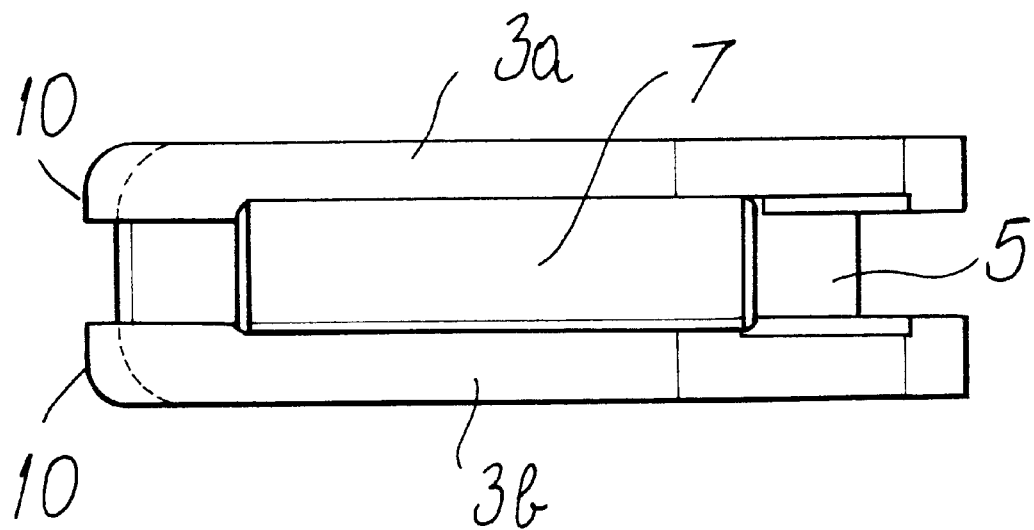

With particular reference to the above figures, the reference numeral 1 generally designates a device for after-use protection of a hypodermic needle A, particularly of the butterfly type, according to the invention: the needle A has an end which is connected to a tube T and has, at its two sides, two grip wings a1 and a2 made of a material such as substantially soft plastics.

The device 1 is constituted by an elongated and substantially rectangular flat laminar element 2 which has, at one of its two short ends, two lateral laminas 3a and 3b which are mutually spaced by a longitudinal central space and are folded, at one end, at 180 degrees toward the upper surface of the element 2 and form two blind lateral flat guides 4a, 4b; the two wings a1, a2 of the needle can slide along the guides 4a, 4b.

The guides 4a, 4b, in their blind region, are slightly curved upward away from the surface of the element 2; when the needle retracts, they are adapted to raise the wings and point the needle with its free end downward, so as to press its point so that it slides against the surface of the central band 5 of the flat element 2 in order to wedge into the bottom of the space provided between raised portions (or teeth) 6a, 6b which are formed in the central band 5 and prevent the escape of the needle.

The edge of a curved profiled element 7 shaped like a cylindrical sector is rigidly coupled along the inner side of the lamina 3a, partially surmounts the lamina 3b and is spaced from it so as to form a longitudinal slot 7a for the insertion of the tube T from one side.

The curved profiled element 7, in addition to acting as a hook for inserting the device from one side of the tube T, also prevents, at the tip of the needle, when said needle is inserted in the device, access with one's fingers to the tip of the needle or to any blood which may have leaked out of the needle.

Advantageously, the free ends 10 of the laminas are curved upward away from the laminar element 2 in order to facilitate the insertion of the wings of the needle.

Likewise, the end 8 of the lower element 2 has an inclination which corresponds to the inclination of the needle in a vein, so that when the needle is extracted its angle does not vary, avoiding stresses to the vein. As seen in FIG. 1, 2b and 2c, the end 8 of the lower element 2 has a central cutout 8a arranged between a pair of lateral teeth 9a, 9b.

The operation of the device 1 is as follows: after gripping the device, the edge of the laminar element 2 is placed under the tube of the needle, the tube T is inserted from the side into the longitudinal slot 7a under the curved profiled element 7, and the device is made to slide until the wings a1, a2 of the needle enter the guides 4a and 4b; in this configuration it is possible to press with the wad of cotton wool against the skin at the needle insertion point, which is exposed; by pulling the tube with just one hand, the needle can be retracted and its point can be made to slide along the central band 5, while the wings a1, a2 of the needle, by sliding along the guides up to their blind end, move slightly away from the element 2 in an upward direction, pushing the tip of the needle against one of the teeth 6a and 6b, depending on the length of the needle: the needle is prevented from escaping by the fact that the tip stops, according to its length, in a gap formed between two teeth 6 by way of the lifting action of the wings of the needle in the guides 4a and 4b.

The device can be provided (FIGS. 4 and 5) so as to use needles which are not of the butterfly type by providing it with adequate dimensions as regards the distance between the laminas 3a and 3b and as regards the lateral guides 4a and 4b.

Conveniently, the invention is provided by molding materials such as plastics and can also be obtained in two substantially symmetrical portions which are mutually joined by gluing or thermal or chemical bonding along a longitudinal centerline or can be obtained monolithically.

The upper surface of the longitudinal central space of the laminar element 2 can be flat or rise slightly at the rear end of the laminas and follow the spacing profile of the guides 4a and 4b.

It has thus been observed that the invention achieves the intended aim and object and in particular that it does not have to be pre-fitted on the tube at the factory but can be fitted without any problem even just before extracting the needle, and that it entails, for use, performing elementary movements which are easy even if they are performed with just one hand; it also allows to effectively press with the cotton wool or the like against the skin area perforated by the needle during its extraction.

The invention thus conceived is susceptible of numerous modifications and variations, all of which are within the scope of the inventive concept.

All the details may also be replaced with other technically equivalent elements.

In practice, the materials employed, as well as the shapes and the dimensions, may be any according to requirements without thereby abandoning the scope of the protection of the appended claims.

The disclosures in Italian Patent Application No. BO98A000572 from which this application claims priority are incorporated herein by reference.

What is claimed is:

1. A device for after-use protection of a hypodermic needle, particularly of a butterfly type, comprising an elongated flat laminar element having, at one end and on two sides, two laminas which are mutually spaced by a longitudinal central band and are folded toward the laminar element in order to form two blind lateral guides for a sliding of butterfly wings of the needle, said blind lateral guides being slightly curved away from a surface of the laminar element and being adapted, when the needle retracts, to press a point of the needle so that said point slides against a surface of the central band of the laminar element in order to wedge into spaces that lie between raised saw-toothed teeth on said central band in order to prevent escape of the needle.

2. The device according to claim 1, wherein an edge of a curved profiled element is rigidly coupled to an inner side of one of said laminas, partially surmounts the other lamina and is spaced from the other lamina so as to form a longitudinal slot for an insertion of a tube of the needle from one side.

3. The device according to claim 2, wherein said curved profiled element that partially surmounts the other lamina is present at least in a region where a tip of the needle is located when said needle is inserted in a safe position on the device according to the invention.

4. The device according to claim 1, wherein free ends of said laminas curve slightly away from the laminar element in order to facilitate insertion of wings of the needle.

5. The device according to claim 4, wherein a distance between a free end of a lower lamina and a curved part of said guides is greater than a length of the needle.

6. The device according to claim 5, wherein the end of the lower element has an inclination which corresponds to an inclination of the needle in a vein.

\* \* \* \* \*